United States Patent [19]

Axelgaard et al.

[11] Patent Number: 4,708,149

[45] Date of Patent: Nov. 24, 1987

[54] ELECTRICAL STIMULATION ELECTRODE

[75] Inventors: Jens Axelgaard, 1104-B Victoria St., Costa Mesa, Calif. 92627; Theodore Grussing, Huntington Beach, Calif.

[73] Assignee: Jens Axelgaard, Fallbrook, Calif.

[21] Appl. No.: 822,816

[22] Filed: Jan. 27, 1986

Related U.S. Application Data

[62] Division of Ser. No. 745,018, Jun. 14, 1985.

[51] Int. Cl.$^4$ .............................................. A61N 1/04
[52] U.S. Cl. .................................... 128/798; 128/802; 29/877; 428/256
[58] Field of Search ................................. 29/877–880; 128/640, 639, 641, 798, 802, 803; 156/148, 289; 428/230, 247, 256

[56] References Cited

U.S. PATENT DOCUMENTS

| | | | |
|---|---|---|---|
| 1,989,282 | 1/1935 | Kimble et al. | 128/798 |
| 3,972,329 | 8/1976 | Kaufman | 128/641 |
| 3,993,049 | 11/1976 | Kater | 128/640 |
| 4,066,078 | 1/1978 | Berg | 128/641 |
| 4,092,985 | 6/1978 | Kaufman | 128/802 |
| 4,239,046 | 12/1980 | Ong | 128/798 |
| 4,243,051 | 1/1981 | Wittemann | 128/798 |
| 4,300,575 | 11/1981 | Wilson | 128/798 |
| 4,458,696 | 7/1984 | Larimore | 128/640 |

FOREIGN PATENT DOCUMENTS

| | | |
|---|---|---|
| 51031 | 6/1911 | Austria . |
| 372002 | 8/1983 | Austria . |
| 2059 | 11/1978 | European Pat. Off. . |
| 29245 | 5/1981 | European Pat. Off. . |
| 2029430 | 9/1973 | Fed. Rep. of Germany . |
| 2023919 | 4/1976 | Fed. Rep. of Germany . |
| 2552197 | 5/1976 | Fed. Rep. of Germany . |
| 750222 | 8/1933 | France . |

Primary Examiner—Percy W. Echols
Attorney, Agent, or Firm—Walter A. Hackler

[57] ABSTRACT

A transcutaneous nerve and/or muscle stimulation electrode is provided which may be contoured to the skin areas of a patient and stretched therewith while impulse signals are electrically conducted into the body. This stretching ability is provided by a knit conductive fabric which is stretchable up to at least about 20% greater than the original conductive fabric dimension in a direction of stretch without loss of conductivity. A conductivity adhesive fills interstitial areas of the knit fabric and provides for adhering the electrode to the patient's skin.

6 Claims, 6 Drawing Figures

ELECTRICAL STIMULATION ELECTRODE

This application is a continuation, of application Ser. No. 745,018, filed June 14, 1985.

The present invention generally relates to electrodes and, more particularly, to electrodes suitable for transcutaneous nerve and/or muscle stimulation.

Continued development of electrical medical devices has produced a need for a variety of electrodes.

Although many of these electrodes have, as a design objective, good electrical signal transmission between a patient's skin surface and electrical leads interconnected with a device, each has specific requirements dependent upon the type of apparatus for which it is to be used.

As an example, electrocardiograph (EKG) and electroencephalograph (EEG) machines are primarily monitoring type device which require small contact surfaces, or area, with the patient's skin.

On the other hand, transcutaneous electric nerve stimulation, (TENS) and muscle stimulation devices require relatively large skin surface contact to effect such nerve and muscle stimulation.

Transcutaneous electrical nerve stimulation is useful, for example, in post-operative and chronic pain control, while muscle stimulation is useful, for example, in maintaining and development of muscle tissue. Electrodes suitable for use in nerve and muscle stimulation preferably provide a uniform electrical coupling across the skin electrode interface.

As hereinbefore noted, electrodes suitable for nerve and/or muscle stimulation may be relatively large having dimensions of several inches or more.

Because nerve and/or muscle stimulation causes muscle contraction, a considerable amount of skin movement is associated therewith.

Additionally, perspiration from the skin is more likely to loosen or disrupt the electrode because of its large size. As should be apparent, the larger the electrode, the longer the evaporation path, or distance, the perspiration occurring at the center regions of the electrode must travel in order to evaporate, or be released to the atmosphere.

It has been found that prior art electrodes which have been secured to the surface of a patient's skin with medical adhesive tape, or the like, have a tendency to lift off from the skin because of perspiration and movement of the patient's skin during treatment.

Because an electrode suitable for nerve and/or muscle stimulation must provide for an electrical signal to be distributed over the entire surface of the electrode, the electrode must necessarily be conductive.

Prior art electrodes have utilized a number of conductive elements, such as carbon impregnated rubber and vinyl, as well as metallic foils.

However, a useful electrode must be flexible in order to accommodate relative movement of the patient's skin therebeneath, as hereinabove-described.

Because nerve and muscle stimulation electrodes may be utilized over a long period of time, as may be necessary in connection with sports injuries, the electrode must be compatible with the skin and flex therewith.

Insufficient flexing of the electrode can result in severe irritation of the patient's skin and electrical "hot spots" due to uneven electrode-skin contact, which manifests itself in a rash and a burning sensation.

The sensation of burning may be sensed by the patient within a few minutes after application of electrical signals during nerve and/or muscle stimulation, while the rash conditions generally take a longer period of time to develop.

It has been found that the use of prior art electrodes in nerve and/or muscle stimultion results in a skin rash in up to 25% to 35% of the people undergoing treatment.

An additional problem associated with the necessary stretchability of electrodes utilized in nerve and/or muscle stimulation procedures is that while the electrode must be able to flex, or stretch, in order to accommodate skin movement during treatment, the conductivity of the electrode should not be interrupted, or distorted, due to the stretching of the electrode.

Prior art electrodes have compromised the flexibility of the electrode in an effort to provide uniform current densities over the entire contact area of the electrode. These electrodes typically utilize a metallic mesh, or foil, to provide contactivity of the electrode and utilize a conductive gel between the electrode and the patient's skin in order to accommodate movement therebetween.

There is, however, relative movement between the relatively rigid electrode and the skin, which is accommodated for by the gel. This relative movement oftentimes causes the gel to move from beneath the conductive portion of the electrode, thereby limiting the useful life of the electrode of the skin.

In addition, this relative motion between the skin and the electrode does not provide for the maintenance of the position of the electrode relative to the nerve and/or muscle being stimulated.

Precision positioning of the electrode is, of course, performed by a physician, or the like, knowledgeable in the treatment method. Inaccurate placement of the electrode, or slipping of the electrode from its intended position, may significantly reduce the beneficial effects of the treatment.

Hence, there is a need for a flexible electrode for use with electrical stimulation devices which adheres well to the patient's skin, is easily removed therefrom, and is able to move with the patient's skin in order to ensure proper continuous placement of the electrode relative to nerve or muscle tissue being stimulated, as well as providing long-term continuous electrical connection therewith without irritation of the skin or discomfort to the patient under treatment. The electrode of the present invention fulfills these needs.

SUMMARY OF THE INVENTION

A flexible transcutaneous electrical nerve and/or muscle stimulation electrode in accordance with the present invention includes a conductive fabric comprising a knit of conductive fiber, the conductive fabric being knit in a fashion which allows for the fabric to be stretched at least up to about 20 percent greater than the original conductive dimension in the direction of the stretch.

Flexible conductive adhesive means are provided and disposed on one side of the conductive fabric for adhering the flexible transcutaneous electrical nerve and/or muscle stimulation electrode to the skin of the patient and providing an electrical conducting contact therebetween.

Interconnection with an electrical stimulation device is provided by means of an electrical lead wire, which is interconnected with the conductive fiber and adapted for interconnection with the electrical stimulation device.

A non-conductive sheet is disposed on the other side of the conductive fabric for preventing undesired electrical contact therewith.

More particularly, the conductive fabric comprises a honeycomb latch needle knit which is capable of being stretched up to about 100 percent greater than a first original conductive fabric dimension and capable of being stretched up to about 20 percent greater than a second original conductive fabric dimension.

Utilization of this knit enables significant stretching of the electrode without a decrease in the conductivity of the fabric. The resulting flexible transcutaneous electrical nerve and/or muscle stimulation electrode has more stretch in one direction than in an opposite orthogonal direction, however, during use, the primary motion of the skin beneath the electrode as a result of a nerve and/or muscle stimulation is, in one direction, along which the primary stretch direction of the electrode is aligned.

Conductivity of the conductive fabric is provided by the conductive fiber which may include a blend of stainless steel and polyester, with the stainless comprising about 20 percent by weight of the result in fiber and the polyester comprising about 80 percent by weight of the conductive fiber.

The non-conductive sheet may be any suitable stretchable plastic, which is held against the conductive fabric by means of a pressure sensitive adhesive.

The non-conductive sheet and the pressure sensitive adhesive are also operative for holding the electrical wire lead against the conductive fabric to provide electrical contact therebetween. This contact is enhanced by utilizing a stranded electrical load wire, which may be stainless steel, and fraying an end portion thereof to thereby provide greater contact area between the electrical lead and the conductive fabric.

DESCRIPTION OF THE DRAWINGS

The advantages and features of the present invention will be better understood by the following description and drawings in which.

DETAILED DESCRIPTION

Figure 1:
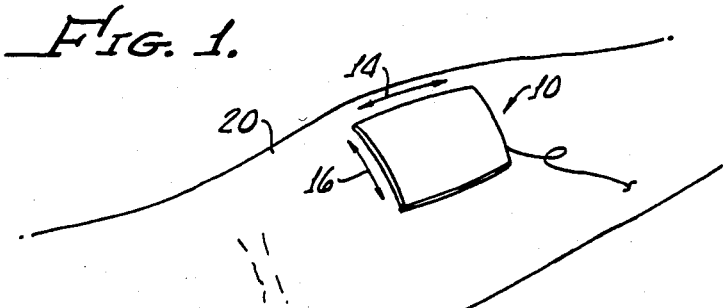
FIG. 1 is a perspective view of a flexible transcutaneous electrical nerve and/or muscle stimulation electrode in accordance with the present invention showing its disposition on a patient's skin.
Figure 2:
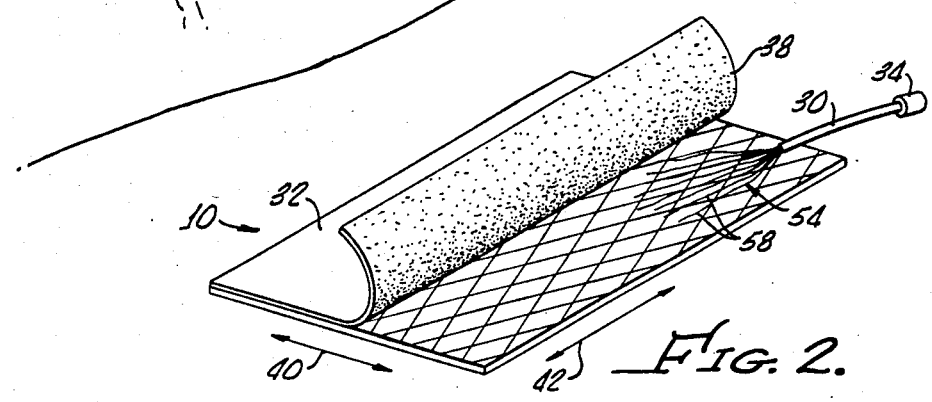
FIG. 2 is a perspective view of the stimulation electrode with a portion of a non-conductive sheet thereof peeled back to show an electrical lead wire therein.

Turning now to FIGS. 1 and 2, there is shown, in perspective view, a flexible transcutaneous electrical nerve and/or muscle stimulation electrode 10 in accordance with the present invention.

As shown in FIG. 1 and hereinafter described in greater detail, the electrode 10 is flexible in two directions, as indicated by arrows 14, 16, while in place on a patient's limb 20, or body, hot shown. As more clearly shown in FIG. 3, the electrode 10 includes a stretchable conductive fabric 22, flexible conductive adhesive 24, which is disposed on one side 28 of the conductive fabric 22 for adhering the flexible transcutaneous electrical nerve and/or muscle stimulation electrode 10 to the skin of a patient (not shown in FIG. 3) and electrical lead wire 30 interconnected with the conductive fibric 22 as hereinafter described, for providing electrical signals to the conductive fabric 22 when interconnected with an electrical stimulation device, not shown, by means of a connector 34, or the like.

In addition, a non-conductive sheet, such as a flexible plastic 32 disposed on another side 36 of the conductive fabric 22 by means of a pressure sensitive adhesive 38, provides means for preventing undesired electrical contact with the conductive fabric 22, as may occur during wearing of the device.

It should be appreciated that the conductive fabric 22 must be isolated from outside objects and other areas of the patient's skin in order to preferentially couple electrical signals into the patient's body where prescribed by an attending physician.

Figure 4:
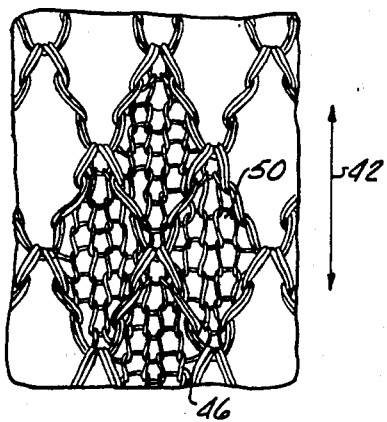
FIG. 4 is an enlarged view of the conductive fabric utilized in the present invention generally showing a honeycomb latch needle knit.
Figure 5:
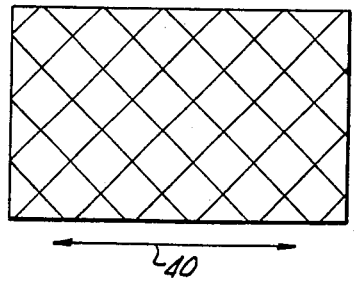
FIG. 5 is an illustration of the conductive fabric utilized in the present invention stretched in a transverse direction.
Figure 6:
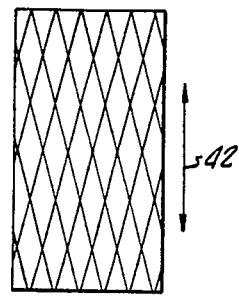
FIG. 6 is an illustration of the conductive fabric utilized in the present invention stretched in a longitudinal direction.

It has been found that a knit fabric, preferably a one-quarter-inch honeycomb latch needle knit fabric, as depicted in FIG. 4, provides for a fabric which may be stretched up to about 100 percent greater than a first original conductive fiber dimension in the direction of stretch, see arrow 40 and FIG. 5, and up to about 20 percent greater than a second original fabric dimension in a second direction of stretch, see arrow 42 and FIG. 6, without loss of conductivity of the fabric. Knits of this nature are commercially available from knitters, such as, for example, Paragon West Knitting Mill in Anaheim Hills, Calif.

The conductivity of the fabric is provided by the individual conductive fibers 46. It has been found that a conductive fiber manufactured by Bakaert of West Germany, which includes a blend of 20 percent 316 stainless steel and 80 percent of polyester when latch needle honeycomb knitted to a density of about 2.5 pounds per square yard, produces a conductive double-stretch knit which is particularly suitable for transcutaneous nerve and/or muscle stimulation electrodes.

The double-stetch nature of this fabric, when incorporated into the electrode of the present invention, as hereindescribed, provides for an electrode which is contourable to the shape of a patient's body or limb.

This is particularly important with relatively large stimulation/electrodes in accordance with the present invention. The electrode 10 may have dimensions in the range of, for example, 2 inches by 3 inches, hence, the electrode must be "fitted" by stretching of the electrode 10 to the skin 20 of a patient in order to provide a uniform contact therebetween.

It is particularly important that the electrode 10 and, of course, the conductive fabric 22, do not degrade during constant and repetitious movement and stretching thereof, as the electrical signals activate muscles and nerves within the patient's body which result in continued movement, or contraction, of the skin. Because the conductive fabric is a loose knit, stretching thereof does not deteriorate any of the conductive fibers therein to any substantial degree, thus causing loss of conductivity of the electrode.

In order to be effective in transmitting electrical signals to the patient's skin 20, the electrode 10 utilizes a conductive adhesive 24, such as one manufactured by Valley Lab, Inc., of Boulder, Colo. under the name Polyhesive, this proprietary product is useful in a number of electrode applications and has the advantage of being flexible so that it will move with the conductive fabric without losing contact with the patient's skin, or interrupting the electrical signals transmitted therethrough.

In the manufacture of the electrode 10, the conductive adhesive 24 is poured onto the surface 28 in a liquid form, whereupon it fills the interstitial areas 50 of the conductive fabric 22.

Thereafter, the adhesive is set into a gel-like material, which has good adhesion to the patient's skin, and is releasable therefrom without the annoyance of hair-pulling and the like. The conductive adhesive 24 is commercially available and is compatible with the skin in that it produces no irritation thereof.

Because the Polyhesive conductive adhesive 24 is in itself flexible, it does stretch with the conductive fabric between the interstitial areas 50 defined by the fibers 46.

Figure 3:
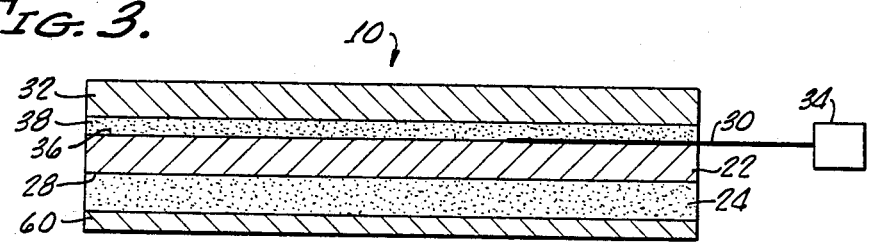
FIG. 3 is a cross-sectional view of the transcutaneous electrical nerve and/or muscle stimulation electrode generally showing conductive fabric, a flexible conductive adhesive, electrical lead wire, non-conductive sheet and a pressure sensitive adhesive.

Turning to FIG. 2 and 3, the non-conductive plastic, or backing layer, 32 is adhered to the other side 36 of the conductive fabric 22, and both the backing layer and the pressure sensitive adhesive 38 hold the lead wire 30 in physical and electrical contact with the conductive fabric. In order to enhance contact therebetween, the conductive lead 30, which may be stranded stainless steel, has an end portion 54 which is frayed and spread apart slightly.

In manufacture, the conductive lead is placed on the conductive fabric 22 for a distance of about onethird the length thereof. Thereafter, the backing layer 32, with adhesive 38 applied thereto, may be firmly placed over the frayed portion 54 and bonded by pressure applied thereto.

This relatively simple method of contacting the lead wire 30 with the conductive fabric 22 enables some movement therebetween as the conductive fiber and electrode stetch.

It should be appreciated that stretching along the direction 40, the major direction of stretch, may stretch the frayed strands 58 apart from one another, thus reducing the relative motion between the frayed end of 54 and the conductive fiber 22.

Because the conductive adhesive 24 is subject to drying, a release liner 60 may be provided for storage of the electrode before and after use. This liner may be of any suitable plastic, or silicon-coated paper, which is strippable from the conductive adhesive 24 without disturbing the integrity of the conductive adhesive.

Although there has been hereinabove-described a specific arrangement of a flexible transcutaneous electrical nerve and/or muscle stimulation electrode in accordance with the invention for the purpose of illustrating the manner in which the invention may be used to advantage, it will be appreciated that the invention is not limited thereto. Accordingly, any and all modifications, variations, or equivalent arrangements which may occur to those skilled in the art, should be considered to be within the scope of the invention as defined in the appended claims.

What is claimed is:

1. A flexible transcutaneous electrical nerve and/or muscle stimulation electrode produced by a method comprising the steps of:
   knitting a conductive fiber to form a conductive fabric having a rhombus shaped pattern of twisted conductive fibers with an open knit of conductive fibers therebetween for supporting a conductive adhesive in interstitial areas therein;
   disposing a flexible conductive adhesive within said interstitial areas and on one side of the conductive fabric;
   interconnecting an electrical lead wire with said conductive fabric; and
   disposing a non-conductive sheet on an opposite side of said conductive fabric.

2. The flexible transcutaneous electrical nerve and/or muscle stimulation electrode according to claim 1 wherein the conductive fiber is knitted for enabling the conductive fabric to be stretched up to about 100 percent greater than a first original conductive fabric dimension parallel to a smaller of the two rhombus diagonals.

3. The transcutaneous electrical nerve and/or muscle stimulation electrical according to claim 2 wherein the conductive fiber is knitted for enabling the conductive fabric to be stretched up to about 20 percent greater than a second original conductive fabric dimension parallel to a larger of the two rhombus diagonals.

4. A flexible transcutaneous electrical nerve and/or muscle stimulation electrode produced by a method comprising the steps of:
   knitting a conductive fiber to form a conductive fabric having a rhombus shaped pattern of twisted conductive fibers with an open knit of conductive fibers therebetween for supporting a conductive adhesive in interstitial areas therein;
   pouring a gellable liquid conductive adhesive within said interstitial areas and on one side of said conductive fabric;
   causing said gellable liquid adhesive conductive adhesive to form into a gel-like conductive adhesive;
   interconnecting an electrical lead wire to the conductive fabric; and,
   disposing a non-conductive sheet on an opposite side of the conductive fabric.

5. A method for the manufacture of a muscle and/or nerve stimulation electrode comprising the steps of;
   knitting a conductive fiber to form a conductive fabric having a rhombus shaped pattern of twisted conductive fibers with an open knit of conductive fibers therebetween for supporting. a conductive adhesive in interstitial areas therein;
   disposing a flexible conductive adhesive within said interstitial areas and on one side of the conductive fabric;
   interconnecting an electrical lead wire with said conductive fabric; and
   disposing a non-conductive sheet on an opposite side of said conductive fabric.

6. A method for the manufacture of a muscle and/or nerve stimulation electrode comprising the steps of:
   knitting a conductive fiber to form a conductive fabric having a rhombus shaped pattern of twisted conductive fibers with an open knit of conductive fibers therebetween for supporting a conductive adhesive in interstitial areas therein;
   pouring a gellable liquid conductive adhesive within said interstitial areas and on one side of said conductive fabric;
   causing said gellable liquid adhesive conductive adhesive to form into a gel-like conductive adhesive;
   interconnecting an electrical lead wire to the conductive fabric; and,
   disposing a non-conductive sheet on an opposite side of the conductive fabric.

* * * * *